(12) United States Patent
McCall

(10) Patent No.: US 8,471,081 B2
(45) Date of Patent: Jun. 25, 2013

(54) PRODUCTION OF DIESEL FUEL FROM CRUDE TALL OIL

(75) Inventor: Michael J. McCall, Geneva, IL (US)

(73) Assignee: UOP LLC, Des Plaines, IL (US)

( * ) Notice: Subject to any disclaimer, the term of this patent is extended or adjusted under 35 U.S.C. 154(b) by 715 days.

(21) Appl. No.: 12/701,236

(22) Filed: Feb. 5, 2010

(65) Prior Publication Data

US 2011/0160505 A1   Jun. 30, 2011

Related U.S. Application Data

(60) Provisional application No. 61/290,402, filed on Dec. 28, 2009.

(51) Int. Cl.
*C07C 1/00* (2006.01)

(52) U.S. Cl.
USPC .............................. 585/240; 585/242; 44/605

(58) Field of Classification Search
CPC . Y02E 50/10; Y02E 50/13; Y02E 50/14; Y02E 50/30; C10G 3/00
USPC .................................... 585/240, 242; 44/605
See application file for complete search history.

(56) References Cited

U.S. PATENT DOCUMENTS

| | | |
|---|---|---|
| 5,186,722 A | 2/1993 | Cantrell et al. |
| 5,705,722 A | 1/1998 | Monnier et al. |
| 7,232,935 B2 | 6/2007 | Jakkula et al. |
| 7,279,018 B2 | 10/2007 | Jakkula et al. |
| 7,288,685 B2 * | 10/2007 | Marker .......................... 585/240 |
| 7,425,657 B1 | 9/2008 | Elliott et al. |
| 7,459,597 B2 | 12/2008 | Koivusalmi et al. |
| 7,491,858 B2 * | 2/2009 | Murzin et al. ................. 585/240 |
| 7,501,546 B2 | 3/2009 | Koivusalmi et al. |
| 7,511,181 B2 * | 3/2009 | Petri et al. ..................... 585/240 |
| 7,540,952 B2 | 6/2009 | Pinho et al. |
| 7,550,634 B2 * | 6/2009 | Yao et al. ....................... 585/240 |
| 7,999,143 B2 | 8/2011 | Marker et al. |
| 2006/0186020 A1 | 8/2006 | Gomes |
| 2006/0207166 A1 | 9/2006 | Herskowitz et al. |
| 2007/0006523 A1 | 1/2007 | Myllyoja et al. |
| 2007/0010682 A1 | 1/2007 | Myllyoja et al. |
| 2007/0068848 A1 | 3/2007 | Monnier et al. |

(Continued)

FOREIGN PATENT DOCUMENTS

| CN | 11270300 A | 9/2008 |
|---|---|---|
| CN | 11343552 A | 1/2009 |

(Continued)

OTHER PUBLICATIONS

"Designs on Engineering Renewable Technology..." Nov. 21, 2005, Thisdell, Glenda: European Chemical News; vol. 83 2172, pp. 31-31.

(Continued)

*Primary Examiner* — Nina Bhat
(74) *Attorney, Agent, or Firm* — Maryann Maas

(57) ABSTRACT

A process has been developed for producing diesel fuel from crude tall oil. The process involves treating a renewable feedstock by hydrogenating and deoxygenating to provide a diesel boiling range fuel hydrocarbon product. If desired, the hydrocarbon product can be isomerized to improve cold flow properties. A portion of the hydrocarbon product is recycled to the treatment zone to increase the hydrogen solubility of the reaction mixture.

16 Claims, 2 Drawing Sheets

U.S. PATENT DOCUMENTS

| | | |
|---|---|---|
| 2007/0130820 A1 | 6/2007 | Chatterjee et al. |
| 2007/0131579 A1 | 6/2007 | Koivusalmi et al. |
| 2007/0135316 A1 | 6/2007 | Koivusalmi et al. |
| 2007/0135663 A1 | 6/2007 | Aalto et al. |
| 2007/0161832 A1 | 7/2007 | Myllyoja et al. |
| 2007/0170091 A1 | 7/2007 | Monnier et al. |
| 2007/0175795 A1 | 8/2007 | Yao et al. |
| 2007/0260102 A1 | 11/2007 | Duarte Santiago et al. |
| 2007/0281875 A1 | 12/2007 | Scheibel et al. |
| 2007/0287873 A1 | 12/2007 | Coupard et al. |
| 2007/0299291 A1 | 12/2007 | Koivusalmi |
| 2008/0025903 A1 | 1/2008 | Cortright |
| 2008/0033188 A1 | 2/2008 | Dumesic et al. |
| 2008/0045731 A1 | 2/2008 | Zhang |
| 2008/0050792 A1 | 2/2008 | Zmierczak et al. |
| 2008/0052983 A1 | 3/2008 | Aulich et al. |
| 2008/0066374 A1 | 3/2008 | Herskowitz |
| 2008/0092436 A1 | 4/2008 | Seames et al. |
| 2008/0132435 A1 | 6/2008 | Ferreira Fontes et al. |
| 2008/0156694 A1 | 7/2008 | Chapus et al. |
| 2008/0161614 A1 | 7/2008 | Bertoncini et al. |
| 2008/0161615 A1 | 7/2008 | Chapus et al. |
| 2008/0163543 A1 | 7/2008 | Abhari et al. |
| 2008/0173570 A1 | 7/2008 | Marchand et al. |
| 2008/0216391 A1 | 9/2008 | Cortright et al. |
| 2008/0229654 A1 | 9/2008 | Bradin |
| 2008/0244962 A1 | 10/2008 | Abhari et al. |
| 2008/0281134 A1 | 11/2008 | Ghonasgi et al. |
| 2008/0300434 A1 | 12/2008 | Cortright et al. |
| 2008/0300435 A1 | 12/2008 | Cortright et al. |
| 2008/0302001 A1 | 12/2008 | Koivusalmi et al. |
| 2008/0308457 A1 | 12/2008 | Dindi et al. |
| 2008/0308458 A1 | 12/2008 | Dindi et al. |
| 2008/0312480 A1 | 12/2008 | Dindi et al. |
| 2008/0313955 A1 | 12/2008 | Silva et al. |
| 2009/0014354 A1 | 1/2009 | Knuuttila et al. |
| 2009/0019763 A1 | 1/2009 | Ghonasgi et al. |
| 2009/0025276 A1 | 1/2009 | Tran |
| 2009/0029427 A1 | 1/2009 | Miller |
| 2009/0031617 A1 | 2/2009 | O'Rear |
| 2009/0056201 A1 | 3/2009 | Morgan |
| 2009/0062578 A1 | 3/2009 | Koivusalmi et al. |
| 2009/0069610 A1 | 3/2009 | Roberts, IV et al. |
| 2009/0071872 A1 | 3/2009 | Ginosar et al. |
| 2009/0077866 A1 | 3/2009 | Kalnes et al. |
| 2009/0082606 A1 | 3/2009 | Marker et al. |
| 2009/0084026 A1 | 4/2009 | Miller |
| 2009/0088351 A1 | 4/2009 | Miller |
| 2009/0107033 A1 | 4/2009 | Gudde et al. |
| 2009/0124839 A1 | 5/2009 | Dumesic et al. |
| 2009/0126260 A1 | 5/2009 | Aravanis et al. |
| 2009/0217573 A1 | 9/2009 | Stigsson |
| 2009/0300970 A1 | 12/2009 | Perego et al. |

FOREIGN PATENT DOCUMENTS

| | | | |
|---|---|---|---|
| EP | 1719811 A1 | 8/2006 | |
| EP | 2046917 | 1/2008 | |
| EP | 2046917 A0 | 1/2008 | |
| WO | 2007063874 A1 | 6/2007 | |
| WO | 2007064015 A1 | 6/2007 | |
| WO | 2007064019 A1 | 6/2007 | |
| WO | WO 2007/064019 A1 | 6/2007 | |
| WO | WO 2007063874 A1 | 6/2007 | |
| WO | WO 2007064015 A1 | 6/2007 | |
| WO | 2007125332 A1 | 11/2007 | |
| WO | WO 2007/125332 A1 | 11/2007 | |
| WO | 2007141293 A1 | 12/2007 | |
| WO | WO 2007/141293 A1 | 12/2007 | |
| WO | 2008012415 A2 | 1/2008 | |
| WO | WO 2008/012415 A2 | 1/2008 | |
| WO | 2008020048 A2 | 2/2008 | |
| WO | WO 2008/020048 A2 | 2/2008 | |
| WO | 2008053284 A1 | 5/2008 | |
| WO | WO 2008/053284 A1 | 5/2008 | |
| WO | 2008101945 A1 | 8/2008 | |
| WO | WO 2008/101945 A1 | 8/2008 | |
| WO | 2008105518 A1 | 9/2008 | |
| WO | 2008119895 A2 | 9/2008 | |
| WO | WO 2008/105518 A1 | 9/2008 | |
| WO | WO 2008/119895 A2 | 9/2008 | |
| WO | 2008141830 A1 | 11/2008 | |
| WO | 2008141831 A1 | 11/2008 | |
| WO | WO 2008/141830 A1 | 11/2008 | |
| WO | WO 2008/141831 A1 | 11/2008 | |
| WO | 2008151792 A1 | 12/2008 | |
| WO | 2008152199 A1 | 12/2008 | |
| WO | WO 2008/151792 A1 | 12/2008 | |
| WO | WO 2008/152199 A1 | 12/2008 | |
| WO | 2009004181 A2 | 1/2009 | |
| WO | 2009011639 A2 | 1/2009 | |
| WO | 2009013233 A2 | 1/2009 | |
| WO | WO 2009/004181 A2 | 1/2009 | |
| WO | WO 2009/011639 A2 | 1/2009 | |
| WO | WO 2009/013233 A2 | 1/2009 | |
| WO | 2009020055 A1 | 2/2009 | |
| WO | 2009025542 A1 | 2/2009 | |
| WO | WO 2009/020055 A1 | 2/2009 | |
| WO | WO 2009/025542 A1 | 2/2009 | |
| WO | 2009059819 A1 | 5/2009 | |
| WO | 2009059920 A2 | 5/2009 | |
| WO | WO 2009/059819 A1 | 5/2009 | |
| WO | WO 2009/059920 A2 | 5/2009 | |

OTHER PUBLICATIONS

"Influence of Tall Oil Biodiesel with Mg and Mo based Fuel Additives on Diesel Engine Performance . . .". Nov. 20, 2007, Keskin et al. Biosource Technology 99 (2008) 6434-6438.

"The Effects of Preheated Cottonseed Oil Methyl Ester on the Performance and Exhaust Emissions . . ." Jan. 11, 2008. Aplied Thermal Engineering 28 (2008) 2136-2143.

"Production of Biodiesel from Tall Oil" Demirbas, Energy Sources, Part A: Recovery, Utilization and Environmental Effects 30(20) 2008 pp. 1896-1902, Taylor and Francis, Inc.

"Green Diesel Production from Vegtable Oil", Marker et al. Extended Abstract 2007 AlCHE, UOP LLC, P.O. Box 163, Riverside, IL Refining Process Development, Eni, Milan Italy.

"Prospects for Biodiesel as a Byproduct . . . ". Lee, et al. U.S. Dept. of Forest Biomaterials Science & Engineering, NC State University. Graduate Shool of Energy & Science.

"Biodiesel Production from Tall Oil with Synthesized . . . ". Keskin, et al. Nov. 27, 2006. Fuel 86 (2007) 1139-1143.

"The Possibility of Producing Biodiesel Fuel . . . ". Pu, et al. Chemical Engineering. Paper Engineering & Imaging, Western MI University 1504, 1A. Concord PI. Kalamazoo, MI.

"Evaluation of Tall Oil as a Feedstock for the Productiono f Biodiesel". Neaves, et al., MI State Univ. & Univ. of Louisiana at Lafayette College of Engineering.

"SunPine Developing Tall Oil Refinery for Production of Biodiesel . . . " Dec. 31, 2007, Green Car Congress, http://www.greencarcongress.com/2007/12/sunpine-develop.html.

"SunPine Developing Tall Oil Refinery for Production of Biodiesel . . . " Dec. 31, 2007, Green Car Congress, http://www.greencarcongress.com/2007/12/sunpine-develop.html.

\* cited by examiner

PRODUCTION OF DIESEL FUEL FROM CRUDE TALL OIL

CROSS REFERENCE TO RELATED APPLICATION

This application claims priority from Provisional application Ser. No. 61/290,402 filed Dec. 28, 2009, the contents of which are hereby incorporated by reference in its entirety.

FIELD OF THE INVENTION

This invention relates to a process for producing diesel boiling range hydrocarbons useful as fuel from crude tall oil, a renewable feedstock, which contains free fatty acids, rosin acids and unsaponifiable components. The process involves hydrogenation, decarboxylation, decarbonylation, and/or hydrodeoxygenation and hydroisomerization in two or more steps.

BACKGROUND OF THE INVENTION

As the demand for diesel boiling range fuel increases worldwide there is increasing interest in sources other than petroleum crude oil for producing diesel fuel. One such source is what has been termed renewable sources. Crude tall oil is one example of a renewable source. Crude tall oil is a side produce of the pulp and paper industry and represents a renewable feedstock that does not compete as a food source. The major components in crude tall oil are free fatty acids, rosin acids, and unsaponifiable hydrocarbons.

The Crude tall oil maybe used as the sole feedstock, or may be used in combination with one or more other renewable sources include, but are not limited to, plant oils such as corn, rapeseed, Camelina, Jatropha, canola, soybean and algal oils, animal fats such as tallow, fish oils and various waste streams such as yellow and brown greases and sewage sludge. The common feature of these additional renewable feedstock sources is that they are composed of glycerides and Free Fatty Acids (FFA). Both of these classes of compounds contain aliphatic carbon chains having from about 8 to about 24 carbon atoms. The aliphatic carbon chains in the glycerides or FFAs can be fully saturated or mono-, di-, or poly-unsaturated.

There are reports in the art disclosing the production of hydrocarbons from oils. For example, U.S. Pat. No. 4,300,009 discloses the use of crystalline aluminosilicate zeolites to convert plant oils such as corn oil to hydrocarbons such as gasoline and chemicals such as para-xylene. U.S. Pat. No. 4,992,605 discloses the production of hydrocarbon products in the diesel boiling range by hydroprocessing vegetable oils such as canola or sunflower oil. Finally, US 2004/0230085 A1 discloses a process for treating a hydrocarbon component of biological origin by hydrodeoxygenation followed by isomerization.

Applicants have developed a process which comprises two or more steps to hydrogenate, decarboxylate, decarbonylate, and/or hydrodeoxygenate and then hydroisomerize the crude tall oil feedstock. Although difficult to see or recognize, and unlike other renewable feedstocks, at room temperature, crude tall oil is a multi-phasic material. So applicants process provides a solution to bring the crude tall oil feedstock into a single phase and maintain the single phase in the process.

SUMMARY OF THE INVENTION

The process is for producing a hydrocarbon fraction useful as a diesel boiling range fuel or fuel blending component from a renewable feedstock wherein the renewable feedstock comprises at least crude tall oil. The process comprises first heating and mixing the crude tall oil to provide a homogeneous renewable feedstock. The feedstock is maintained at an elevated temperature while being conducted to and introduced into a reaction zone. The feedstock is treated in the reaction zone by hydrogenating and deoxygenating the renewable feedstock in the presence of a catalyst at reaction conditions to provide a reaction product comprising a hydrocarbon fraction comprising n-paraffins useful as a diesel boiling range fuel, or fuel blending component. A portion of hydrocarbon fraction may be recycled to the reaction zone wherein the volume ratio of recycle to feedstock is in the range of about 2:1 to about 8:1. The hydrogenation and deoxygenation reaction product may be isomerized to provide an isomerized reaction product.

DETAILED DESCRIPTION OF THE INVENTION

Figure 1:
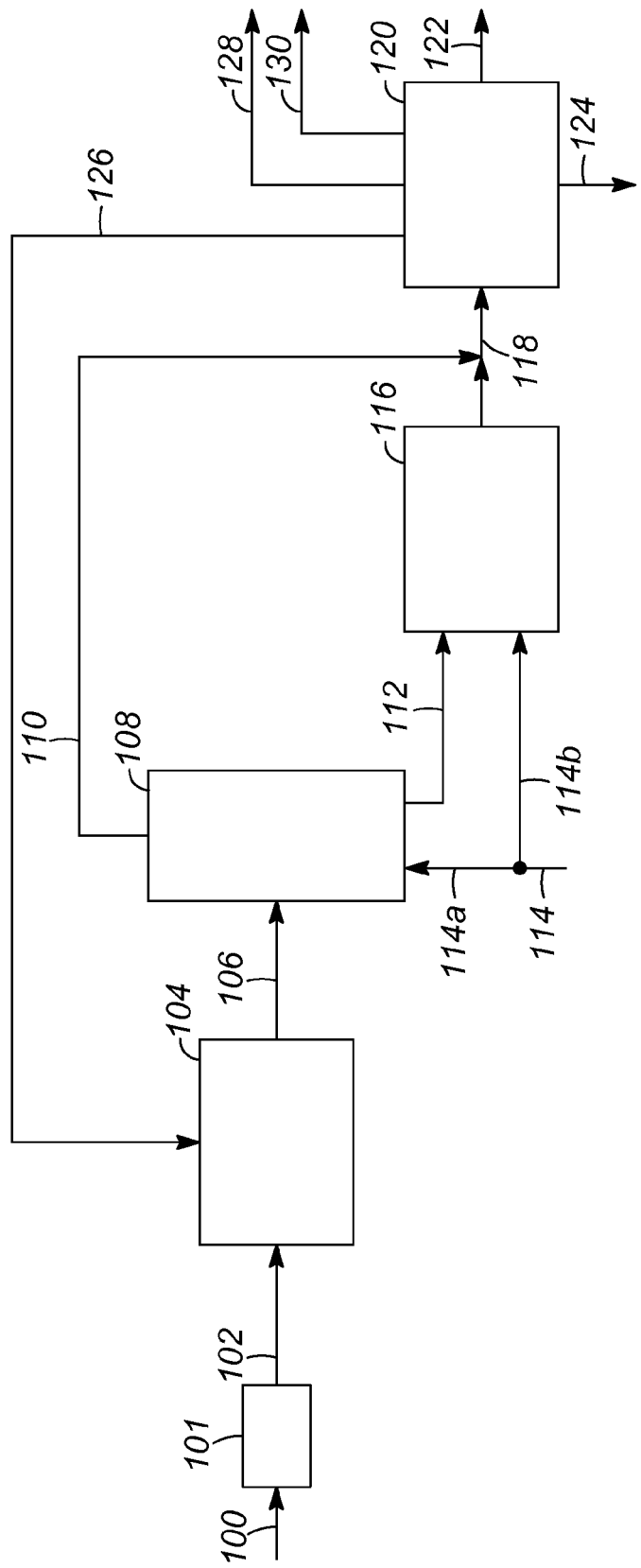
FIG. 1 is a general flow scheme of one embodiment of the invention.

As stated, the present invention relates to a process for producing a hydrocarbon stream useful as diesel boiling range fuel from renewable feedstocks such as those feedstocks originating as by products from the paper and pulp industry, specifically, crude tall oil. Crude tall oil is a renewable raw material originating from wood, which comprises organic compounds that can be converted to combustion engine fuels such as diesel fuel, as well as other potentially valuable products such as resin acids and sterols. The term "crude tall oil" is often used to distinguish the tall oil from tall oil products. Therefore, the terms "crude tall oil" and "tall oil" refer to the same material and will be used interchangeably herein.

Tall oil is a major by-product of the alkaline Kraft pulping process. The tall oil originates from the extractives in the wood raw material. In the pulping process rosin acids (RA) and fatty acids (FA), which occur as free acids or their esters, are saponified by the alkaline cooking liquor to their corresponding sodium salts. These salts, or soaps, along with neutral organic components, often called unsaponifiables, are dissolved and suspended in the spent cooking liquor (black liquor). This liquor is later concentrated and the soaps and neutrals are separated as tall oil soap skimmings Many pulp mills are recovering this soap and after acidulation, a crude tall oil (CTO) is obtained for export or upgrade at the mill. The tall oil recovered from a softwood kraft mill typically consist of approximately 35-60% fatty acids, including oleic, linoleic, linolenic and palmitic acids, 15-55% rosin acids, including abietic, dehydroabietic and neoabietic acids and 5-35% unsaponifiable and neutral material including sterols such as beta-sitosterol. Hardwoods also contain extractives including fatty acids and neutrals (beta-sitosterol, betulin) but no resin acids.

The term renewable feedstock is meant to include feedstocks other than those derived from petroleum crude oil, such as the tall oil described above. Other renewable feedstocks that can be used in combination as mixtures or co-feeds with tall oil in the present invention include any of those which comprise glycerides and free fatty acids (FFA). Most of the glycerides will be triglycerides, but monoglycerides and diglycerides may be present and processed as well.

Examples of these renewable feedstocks include, but are not limited to, canola oil, corn oil, soy oils, rapeseed oil, soybean oil, colza oil, sunflower oil, hempseed oil, olive oil, linseed oil, coconut oil, castor oil, peanut oil, palm oil, mustard oil, cottonseed oil, jatropha oil, camelina oil, tallow, yellow and brown greases, lard, train oil, fats in milk, fish oil, algal oil, sewage sludge, and the like. Additional examples of renewable feedstocks include non-edible vegetable oils from the group comprising Jatropha curcas (Ratanjoy, Wild Castor, Jangli Erandi), Madhuca indica (Mohuwa), Pongamia pinnata (Karanji Honge), and Azadiracta indicia (Neem). The glycerides and FFAs of the typical vegetable or animal fat contain aliphatic carbon chains in their structure which have about 8 to about 24 carbon atoms, with a majority of the fats and oils containing a high concentration of 16 and 18 carbon atom chains. Mixtures or co-feeds of tall oil and petroleum derived hydrocarbons may also be used as the feedstock. Other feedstock components which may be used, especially as a co-feed component in combination with tall oil and the above listed renewable feedstocks, include, spent motor oils and industrial lubricants, used paraffin waxes, liquids derived from the gasification of coal, biomass (including pyrolysis oils), natural gas followed by a downstream liquefaction step such as Fischer-Tropsch technology, liquids derived from depolymerization, thermal or chemical, of waste plastics such as polypropylene, high density polyethylene, and low density polyethylene; and other synthetic oils generated as byproducts from petrochemical and chemical processes. Mixtures of the above feedstocks may also be used as co-feed components. One advantage of using a co-feed component is the transformation of may have been considered to be a waste product from a petroleum based or other process into a valuable co-feed component to the current process.

Renewable feedstocks that can be used in the present invention may contain a variety of impurities. For example, tall oil is a by product of the wood processing industry and tall oil contains esters and rosin acids in addition to FFAs. Rosin acids are cyclic carboxylic acids. The renewable feedstocks may also contain contaminants such as alkali metals, e.g. sodium and potassium, phosphorous as well as solids, water and detergents. An optional first step is to remove at least some of these contaminants. One possible pretreatment step involves contacting the renewable feedstock with an ion-exchange resin in a pretreatment zone at pretreatment conditions. The ion-exchange resin is an acidic ion exchange resin such as Amberlyst™-15 and can be used as a bed in a reactor through which the feedstock is flowed through, either upflow or downflow. Yet another possible means of removing metal contaminants from the feedstock is through the use of guard beds which are well known in the art. These can include alumina guard beds either with or without demetallation catalysts such as nickel or cobalt. Filtration and solvent extraction techniques are other choices which may be employed. Hydroprocessing such as that described in U.S. Pat. No. 7,638,040 is another pretreatment technique which may be employed.

Applicants have found that using tall oil as a feedstock presents unique problems as compared to other renewable feedstocks. The two major components of crude tall oil, rosin acids and fatty acids, separate at low temperatures forming a biphasic feed. The heavier rosin acids settle in the bottom phase and the applicants have found that this phase is more susceptible to thermal polymerization reactions that can deactivate the catalysts. The tall oil feed remains in one phase when heated, and mixing the feed accelerates homogeneity in the presence of heat. The applicants found that preventing phase separation in the feed to be critical for a stable deoxygenation process. Therefore, heating of the tall oil prior to introduction into the reaction zone is critical to the operation of the process. Mixing the tall oil, although not critical, may be important as well. Experiments have shown that the catalyst may be severely deactivated by the tall oil unless the heating step is employed, see Example 1. By comparison, when the tall oil is heated to and maintained at a temperature ranging from about 60° C. to about 80° C. the catalyst did not deactivate, see Example 2. Furthermore, mixing the heated tall oil accelerates feed homogeneity to eliminate component separation.

The mixing may occur at a point prior to the tall oil being conducted to the reaction zone, but the tall oil should be maintained at the elevated temperate of about 60° C. to about 80° C. prior to the reaction zone and while be conducted to the reaction zone. The feed can be heated to a temperature greater than 80° C., but higher temperatures will accelerate degradation of the feed by promoting polymerization reactions. For example, in the experiments, the conduits to the reaction zone were equipped with heat tracing to maintain the conduits in the temperature range of about 60° C. to about 80° C.

The tall oil feedstock is flowed to a reaction zone comprising one or more catalyst beds in one or more reactors. The term feedstock is meant to include feedstocks that have not been treated to remove contaminants as well as those feedstocks purified in a pretreatment zone to remove impurities such as alkali metals. In the reaction zone, the renewable feedstock is contacted with a hydrogenation or hydrotreating catalyst in the presence of hydrogen at hydrogenation conditions to hydrogenate the olefinic or unsaturated portions of the n-paraffinic chains. Hydrogenation or hydrotreating catalysts are any of those well known in the art such as nickel or nickel/molybdenum dispersed on a high surface area support. Other hydrogenation catalysts include one or more noble metal catalytic elements dispersed on a high surface area support. Non-limiting examples of noble metals include Pt and/or Pd dispersed on gamma-alumina. Hydrogenation conditions include a temperature of about 200° C. to about 400° C. and a pressure of about 1379 kPa absolute (200 psia) to about 4826 kPa absolute (700 psia). Other operating conditions for the hydrogenation zone are well known in the art.

The hydrogenation and hydrotreating catalysts enumerated above are also capable of catalyzing decarboxylation, decarbonylation, and/or hydrodeoxygenation of the feedstock to remove oxygen. Decarboxylation, decarbonylation, and hydrodeoxygenation are herein collectively referred to as deoxygenation reactions. Decarboxylation and decarbonylation conditions include a relatively low pressure of about 3447 kPa (500 psia) to about 10,342 kPa (1500 psia), a temperature of about 288° C. to about 345° C. and a liquid hourly space velocity of about 1 to about 4 $hr^{-1}$. Since hydrogenation is an exothermic reaction, as the feedstock flows through the catalyst bed the temperature increases and decarboxylation and hydrodeoxygenation will begin to occur. Thus, it is envisioned and is within the scope of this invention that all three reactions occur simultaneously in one reactor or in one bed. Alternatively, the conditions can be controlled such that hydrogenation primarily occurs in one bed and decarboxylation and/or hydrodeoxygenation occurs in a second bed. Of course if only one bed is used, then hydrogenation occurs primarily at the front of the bed, while decarboxylation, decarbonylation and hydrodeoxygenation occurs mainly in the middle and bottom of the bed. Finally, desired hydrogenation can be carried out in one reactor, while decarboxylation, decarbonylation, and/or hydrodeoxygenation can be carried out in a separate reactor.

Hydrogen is a reactant in the reactions above, and to be effective, a sufficient quantity of hydrogen must be in solution to most effectively take part in the catalytic reaction. Past processes have operated at high pressures in order to achieve a desired amount of hydrogen in solution and readily available for reaction. If hydrogen is not available at the reaction site of the catalyst, the coke forms on the catalyst and deactivates the catalyst. To solve this problem, the pressure is often raised to insure enough hydrogen is available to avoid coking reactions on the catalyst. However, higher pressure operations are more costly to build and to operate as compared to their lower pressure counterparts. One advantage of an embodiment of the present invention is the operating pressure is in the range of about 1379 kPa absolute (200 psia) to about 10342 kPa absolute (1500 psia). In another embodiment the operating pressure is in the range of about 2413 kPa absolute (350 psia) to about 4481 kPa absolute (650 psia), and in yet another embodiment operating pressure is in the range of about 5516 kPa absolute (800 psia) to about 8273 kPa absolute (1200 psia).

The desired amount of hydrogen is kept in solution at lower pressures by employing a large recycle of hydrocarbon. Other processes have employed hydrocarbon recycle in order to control the temperature in the reaction zones since the reactions are exothermic reactions. However, the range of recycle to feedstock ratios used herein is set based on the need to control the level of hydrogen in the liquid phase and therefore reduce the deactivation rate. The amount of recycle is determined not on temperature control requirements, but instead, based upon hydrogen solubility requirements. Hydrogen has a greater solubility in the hydrocarbon product than it does in the feedstock. By utilizing a large hydrocarbon recycle the solubility of hydrogen in the liquid phase in the reaction zone is greatly increased and higher pressures are not needed to increase the amount of hydrogen in solution and avoid catalyst deactivation at low pressures. In one embodiment of the invention, the volume ratio of hydrocarbon recycle to feedstock is from about 2:1 to about 8:1 or from about 2:1 to about 6:1. In another embodiment the ratio is in the range of about 3:1 to about 6:1 and in yet another embodiment the ratio is in the range of about 4:1to about 5:1. The determination of the ranges of suitable volume ratios of hydrocarbon recycle is shown in U.S. Pat. No. 7,982,076, hereby incorporated by reference in its entirety.

The reaction product from the deoxygenation reactions in the deoxygenation zone will comprise a liquid portion and a gaseous portion. The liquid portion comprises a hydrocarbon fraction which is essentially fully deoxygenated and hydrogenated products of the feed molecules, i.e., deoxygenated rosin acids and fatty acids or cycloparaffins and n-paraffins respectively. The hydrocarbons present in the feed will be present in the liquid portions as well. The n-paraffins having carbon numbers in the range of C8 to about C24. Different feedstocks will result in different distributions of paraffins. A portion of this hydrocarbon fraction, after separation, may be used as the hydrocarbon recycle described above. Although this hydrocarbon fraction is useful as a diesel boiling range fuel, or a fuel blending component, because it comprises essentially all n-paraffins, it will have poor cold flow properties. To improve the cold flow properties of the liquid hydrocarbon fraction, the liquid hydrocarbon fraction is contacted with an isomerization catalyst under isomerization conditions to at least partially isomerize the n-paraffins to branched paraffins such as isoparaffins. Catalysts and conditions for isomerization are well known in the art. See for example US 2004/0230085 A1 which is incorporated by reference in its entirety. Isomerization can be carried out in a separate bed of the same reaction zone, i.e. same reactor, described above or the isomerization can be carried out in a separate reactor.

The product of the hydrogenation and deoxygenation reaction zone is contacted with an isomerization catalyst in the presence of hydrogen at isomerization conditions to isomerize the normal paraffins to branched paraffins. Only minimal branching is required, enough to overcome cold-flow problems of the normal paraffins. Since attempting for significant branching runs the risk of high degree of undesired cracking, the predominant isomerized product is a mono-branched hydrocarbon.

The isomerization of the paraffinic product can be accomplished in any manner known in the art or by using any suitable catalyst known in the art. Suitable catalysts comprise a metal of Group VIII (IUPAC 8-10) of the Periodic Table and a support material. Suitable Group VIII metals include platinum and palladium, each of which may be used alone or in combination. The support material may be amorphous or crystalline Suitable support materials include amorphous alumina, amorphous silica-alumina, ferrierite, ALPO-31, SAPO-11, SAPO-31, SAPO-37, SAPO-41, SM-3, MgAPSO-31, FU-9, NU-10, NU-23, ZSM-12, ZSM-22, ZSM-23, ZSM-35, ZSM-48, ZSM-50, ZSM-57, MeAPO-11, MeAPO-31, MeAPO-41, MgAPSO-11, MgAPSO-31, MgAPSO-41, MgAPSO-46, ELAPO-11, ELAPO-31, ELAPO-41, ELAPSO-11, ELAPSO-31, ELAPSO-41, laumontite, cancrinite, offretite, hydrogen form of stillbite, magnesium or calcium form of mordenite, and magnesium or calcium form of partheite, each of which may be used alone or in combination. ALPO-31 is described in U.S. Pat. No. 4,310,440. SAPO-11, SAPO-31, SAPO-37, and SAPO-41 are described in U.S. Pat. No. 4,440,871. SM-3 is described in U.S. Pat. Nos. 4,943,424; 5,087,347; 5,158,665; and 5,208,005. MgAPSO is a MeAPSO, which is an acronym for a metal aluminumsilicophosphate molecular sieve, where the metal Me is magnesium (Mg). Suitable MgAPSO-31 catalysts include MgAPSO-31. MeAPSOs are described in U.S. Pat. No. 4,793,984, and MgAPSOs are described in U.S. Pat. No. 4,758,419. MgAPSO-31 is a preferred MgAPSO, where 31 means a MgAPSO having structure type 31. Many natural zeolites, such as ferrierite, that have an initially reduced pore size can be converted to forms suitable for olefin skeletal isomerization by removing associated alkali metal or alkaline earth metal by ammonium ion exchange and calcination to produce the substantially hydrogen form, as taught in U.S. Pat. Nos. 4,795,623 and 4,924,027. Further catalysts and conditions for skeletal isomerization are disclosed in U.S. Pat. Nos. 5,510,306, 5,082,956, and 5,741,759.

The isomerization catalyst may also comprise a modifier selected from the group consisting of lanthanum, cerium, praseodymium, neodymium, samarium, gadolinium, terbium, and mixtures thereof, as described in U.S. Pat. Nos. 5,716,897 and 5,851,949. Other suitable support materials include ZSM-22, ZSM-23, and ZSM-35, which are described for use in dewaxing in U.S. Pat. No. 5,246,566 and in the article entitled "New molecular sieve process for lube dewaxing by wax isomerization," written by S. J. Miller, in Microporous Materials 2 (1994) 439-449. The teachings of U.S. Pat. Nos. 4,310,440; 4,440,871; 4,793,984; 4,758,419; 4,943,424 ; 5,087,347; 5,158,665; 5,208,005; 5,246,566; 5,716,897; and 5,851,949 are hereby incorporated by reference.

U.S. Pat. Nos. 5,444,032 and 5,608,968 teach a suitable bifunctional catalyst which is constituted by an amorphous silica-alumina gel and one or more metals belonging to Group VIIIA, and is effective in the hydroisomerization of long-chain normal paraffins containing more than 15 carbon atoms. U.S. Pat. Nos. 5,981,419 and 5,908,134 teach a suitable bifunctional catalyst which comprises: (a) a porous crystalline material isostructural with beta-zeolite selected from boro-silicate (BOR-B) and boro-alumino-silicate (Al-BOR-B) in which the molar $SiO_2:Al_2O_3$ ratio is higher than 300:1; (b) one or more metal(s) belonging to Group VIIIA, selected from platinum and palladium, in an amount comprised within the range of from 0.05 to 5% by weight. Article V. Calemma et al., App. Catal. A: Gen., 190 (2000), 207 teaches yet another suitable catalyst.

The isomerization catalyst may be any of those well known in the art such as those described and cited above. Isomerization conditions include a temperature of about 150° C. to about 360° C. and a pressure of about 1724 kPa absolute (250 psia) to about 4726 kPa absolute (700 psia). In another embodiment the isomerization conditions include a temperature of about 300° C. to about 360° C. and a pressure of about 3102 kPa absolute (450 psia) to about 3792 kPa absolute (550 psia). Other operating conditions for the isomerization zone are well known in the art.

The final effluent stream, i.e. the stream obtained after all reactions have been carried out, is now processed through one or more separation steps to obtain a purified hydrocarbon stream useful as a diesel boiling range fuel or fuel blending component. If a single stage process was used for both deoxygenation and isomerization, it is likely that the final effluent stream comprises both a liquid and a gaseous component, and so the liquid and gaseous components are separated using a separator such as a cold separator. If deoxygenation and isomerization were conducted in separate stages, the final effluent stream may not have much of a gaseous component, thus not requiring separation. The liquid component comprises the product hydrocarbon stream useful as a diesel fuel. Further separations may be performed to remove naphtha and LPG from the product hydrocarbon stream. The separated gaseous component comprises mostly hydrogen and the carbon dioxide from the decarboxylation reaction. The carbon dioxide can be removed from the hydrogen by means well known in the art, reaction with a hot carbonate solution, pressure swing absorption, etc. Also, absorption with an amine in processes such as described in co-pending applications U.S. Pat. Nos. 7,982,077 and 7,982,078, hereby incorporated by reference, may be employed. If desired, essentially pure carbon dioxide can be recovered by regenerating the spent absorption media. The hydrogen remaining after the removal of the carbon dioxide may be recycled to the reaction zone where hydrogenation primarily occurs and/or to any subsequent beds/reactors.

Finally, a portion of the product hydrocarbon is recycled to the hydrogenating and deoxygenating reaction zone. The recycle stream may be taken from the product hydrocarbon stream after the hydrogenating and deoxygenating reactor(s) and separation form gaseous components, and recycled back to the hydrogenating and deoxygenating reactor(s). Or the recycle stream may be taken from the effluent of a separation unit, such as a hot high pressure separator, located between the deoxygenation reaction zone and the isomerization reaction zone. Although possible, it is less preferred to take the recycle stream from the isomerized product since isomerized products are more susceptible to cracking than the normal paraffins in the hydrogenating and deoxygenating reaction zone. A portion of a hydrocarbon stream from, for example, a hot high pressure separator or a cold high pressure separator, may also be cooled down if necessary and used as cool quench liquid between the beds of the deoxygenation reaction zone to further control the heat of reaction and provide quench liquid for emergencies. The recycle stream may be introduced to the inlet of the deoxygenation reaction zone and/or to any subsequent beds or reactors. One benefit of the hydrocarbon recycle is to control the temperature rise across the individual beds. However, as discussed above, the amount of hydrocarbon recycle herein is determined based upon the desired hydrogen solubility in the reaction zone. Increasing the hydrogen solubility in the reaction mixture allows for successful operation at lower pressures, and thus reduced cost. Operating with high recycle and maintaining high levels of hydrogen in the liquid phase helps dissipate hot spots at the catalyst surface and reduces the formation of undesirable heavy components which lead to coking and catalyst deactivation. Furthermore, high hydrocarbon recycle operates to dilute any heavy components in the feedstock and avoid formation of gums which plug pre-heaters and the reactor.

The following embodiment is presented in illustration of this invention and is not intended as an undue limitation on the generally broad scope of the invention as set forth in the claims. First an embodiment is described in general as with reference to FIG. 1. Then an embodiment is described in more detail with reference to FIG. 2.

Turning to FIG. 1 renewable feedstock comprising at least tall oil in line 100 enters heater and mixer 101 where the tall oil is brought to a temperature of from about 60° C. to about 80° C. and is mixed. The heated and mixed tall oil feedstock is conducted via line 102 which is equipped to maintain the temperature of the tall oil and enters deoxygenation reaction zone 104 along with recycle hydrogen 126. Deoxygenated product 106 is stripped in hot high pressure hydrogen stripper 108 using hydrogen 114a. Carbon oxides and water vapor are removed with hydrogen in overhead 110. Selectively stripped deoxygenated product is passed to isomerization zone 116 along with recycle hydrogen 126a and make-up hydrogen 114b. Isomerized product 118 is combined with overhead 110 and passed to product recovery zone 120. Carbon oxide stream 128, light ends stream 130, water byproduct stream 124, hydrogen stream 126, and branched paraffin-rich product 122 are removed from product recover zone 120. Branched paraffin-rich product 122 may be collected for use as diesel fuel and hydrogen stream 126 is recycled to the deoxygenation reaction zone 104.

Figure 2:
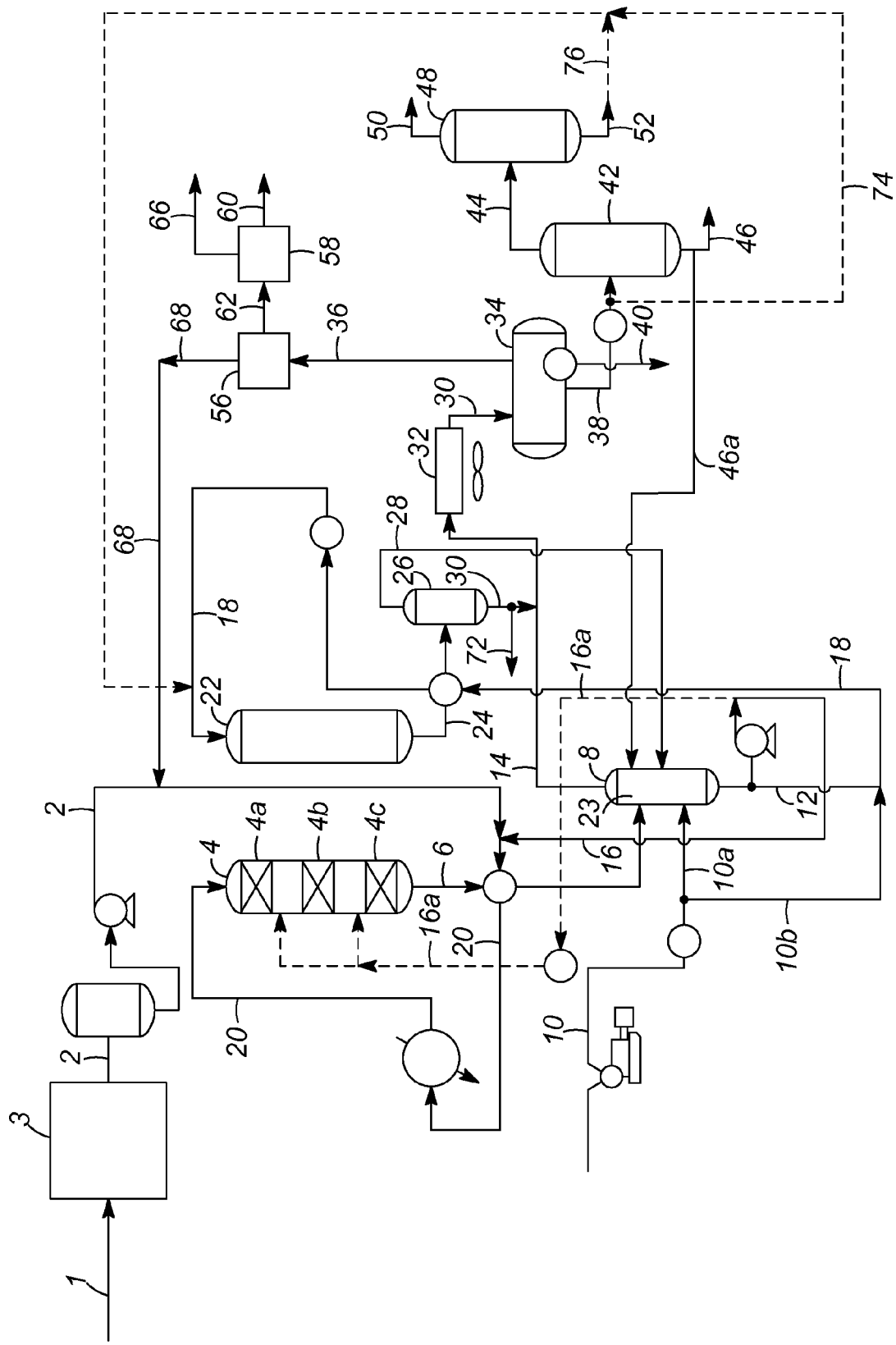
FIG. 2 is a more detailed flow scheme of one embodiment of the invention.

Turning to FIG. 2, the process begins with a tall oil renewable feedstock stream 1 being introduced into mixer-heater 3. The feedstock is mixed and heated to a temperature of from about 60° C. to about 80° C. The mixed and heated feedstock is removed in line 2 and may pass through an optional feed surge drum. Line 2 and the optional feed surge drum are equipped to maintain the temperature of the feedstock at about 60° C. to about 80° C. The feedstock stream in line 2 is combined with recycle gas stream 68 and recycle stream 16 to form combined feed stream 20, which is heat exchanged with reactor effluent and then introduced into deoxygenation reactor 4. Line 20 is also equipped to maintain the temperature of the feedstock at from about 60° C. to about 80° C. The heat exchange may occur before or after the recycle is combined with the feed. Deoxygenation reactor 4 may contain multiple beds shown in FIG. 2 as 4a, 4b and 4c. Deoxygenation reactor 4 contains at least one catalyst capable of catalyzing decarboxylation and/or hydrodeoxygenation of the feedstock to remove oxygen. Deoxygenation reactor effluent stream 6 containing the products of the decarboxylation and/or hydrodeoxygenation reactions is removed from deoxygenation reactor 4 and heat exchanged with stream 20 containing feed to the deoxygenation reactor. Stream 6 comprises a liquid component containing largely cycloparaffins and normal paraffin hydrocarbons in the diesel boiling range and a gaseous component containing largely hydrogen, vaporous water, carbon monoxide, carbon dioxide and light ends.

Deoxygenation reactor effluent stream 6 is then directed to hot high pressure hydrogen stripper 8. Make up hydrogen in line 10 is divided into two portions, stream 10a and 10b. Make up hydrogen in stream 10a is also introduced to hot high pressure hydrogen stripper 8. In hot high pressure hydrogen stripper 8, the gaseous component of deoxygenation reactor effluent 6 is selectively stripped from the liquid component of deoxygenation reactor effluent 6 using make-up hydrogen 10a and recycle hydrogen 28. The dissolved gaseous component comprising hydrogen, vaporous water, carbon monoxide, carbon dioxide, and some light hydrocarbons is selectively separated into hot high pressure hydrogen stripper overhead stream 14. The remaining liquid component of deoxygenation reactor effluent 6 comprising primarily of cycloparaffins, normal paraffins, and a smaller amount of aromatics present in the feed. The cycloparaffins have carbon numbers from C6 to C40, predominantly C19 to C20. The normal paraffins having a carbon number from about 8 to about 24, predominately C16 to C20, with a cetane number of about 60 to about 100 is removed as hot high pressure hydrogen stripper bottom 12.

A portion of hot high pressure hydrogen stripper bottoms forms recycle stream 16 and is combined with renewable feedstock stream 2 to create combined feed 20. Another portion of recycle stream 16, optional stream 16a, may be routed directly to deoxygenation reactor 4 and introduced at interstage locations such as between beds 4a and 4b and/or between beds 4b and 4c in order, or example, to aid in temperature control. The remainder of hot high pressure hydrogen stripper bottoms in stream 12 is combined with hydrogen stream 10b to form combined stream 18 which is routed to isomerization reactor 22. Stream 18 may be heat exchanged with isomerization reactor effluent 24.

The product of the isomerization reactor containing a gaseous portion of hydrogen and light hydrocarbons and a liquid hydrocarbon portion is removed in line 24, and after optional heat exchange with stream 18, is introduced into hydrogen separator 26. The overhead stream 28 from hydrogen separator 26 contains primarily hydrogen which may be recycled back to hot high pressure hydrogen stripper 8. Bottom stream 30 from hydrogen separator 26 is air cooled using air cooler 32 and introduced into product separator 34. In product separator 34 the gaseous portion of the stream comprising hydrogen, carbon monoxide, hydrogen sulfide, carbon dioxide and light hydrocarbons are removed in stream 36 while the liquid hydrocarbon portion of the stream is removed in stream 38. A water byproduct stream 40 may also be removed from product separator 34. Stream 38 is introduced to product stripper 42 where components having higher relative volatilities are separated into stream 44 with the remainder, the diesel range components, being withdrawn from product stripper 42 in line 46. Stream 44 is introduced into fractionator 48 which operates to separate LPG into overhead 50 leaving a naphtha bottoms 52. Any of optional lines 72, 74, or 76 may be used to recycle at least a portion of the isomerization zone effluent back to the isomerization zone to increase the amount of n-paraffins that are isomerized to branched paraffins.

The vapor stream 36 from product separator 34 contains the gaseous portion of the isomerization effluent which comprises at least hydrogen, carbon monoxide, hydrogen sulfide, carbon dioxide and light hydrocarbons and is directed to a system of amine absorbers to separate carbon dioxide and hydrogen sulfide from the vapor stream. Because of the cost of hydrogen, it is desirable to recycle the hydrogen to deoxygenation reactor 4, but it is not desirable to circulate the carbon dioxide or an excess of sulfur containing components.

In order to separate sulfur containing components and carbon dioxide from the hydrogen, vapor stream 36 is passed through a system of at least two amine absorbers, also called scrubbers, starting with the first amine absorber zone 56. The amine chosen to be employed in first amine scrubber 56 is capable of selectively removing at least both the components of interest, carbon dioxide and the sulfur components such as hydrogen sulfide. Suitable amines are available from DOW and from BASF, and in one embodiment the amines are a promoted or activated methyldiethanolamine (MDEA). See U.S. Pat. No. 6,337,059, hereby incorporated by reference in its entirety. Suitable amines for the first amine absorber zone from DOW include the UCARSOL™ AP series solvents such as AP802, AP804, AP806, AP810 and AP814. The carbon dioxide and hydrogen sulfide are absorbed by the amine while the hydrogen passes through first amine scrubber zone and into line 68 to be recycled to the first reaction zone. The amine is regenerated and the carbon dioxide and hydrogen sulfide are released and removed in line 62. Within the first amine absorber zone, regenerated amine may be recycled for use again. The released carbon dioxide and hydrogen sulfide in line 62 are passed through second amine scrubber zone 58 which contains an amine selective to hydrogen sulfide, but not selective to carbon dioxide. Again, suitable amines are available from DOW and from BASF, and in one embodiment the amines are a promoted or activated MDEA. Suitable amines for the second amine absorber zone from DOW include the UCARSOL™ HS series solvents such as HS101, HS 102, HS103, HS104, HS115. Therefore the carbon dioxide passes through second amine scrubber zone 58 and into line 66. The amine may be regenerated which releases the hydrogen sulfide into line 60. Regenerated amine is then reused, and the hydrogen sulfide may be recycled to the deoxygenation reaction zone. Conditions for the first scrubber zone includes a temperature in the range of 30 to 60° C. The first absorber is operated at essentially the same pressure as the reaction zone. By "essentially" it is meant that the operating pressure of the first absorber is within about 1034 kPa absolute (150 psia) of the operating pressure of the reaction zone. For example, the pressure of the first absorber is no more than 1034 kPa absolute (150 psia) less than that of the reaction zone. The second amine absorber zone is operated in a pressure range of from 138 kPa absolute (20 psia) to 241 kPa absolute (35 psia). Also, at least the first the absorber is operated at a temperature that is at least 1° C. higher than that of the separator. Keeping the absorbers warmer than the separator operates to maintain any light hydrocarbons in the vapor phase and prevents the light hydrocarbons from condensing into the absorber solvent.

In another embodiment of the invention, the hydrogenation and deoxygenation reaction zone may be combined with the isomerization zone with all reactions taking place in a single stage. Furthermore, the branched paraffins obtained from the renewable source may be blended with hydrocarbons derived from crude oil such as those generated in traditional refining.

The following examples are presented in illustration of this invention and are not intended as undue limitations on the generally broad scope of the invention as set out in the appended claims.

EXAMPLES

Example 1

Deoxygenation of Crude Tall Oil with Non-heated and Non-mixed Feed

The crude tall oil was thoroughly mixed, sampled, and then mixed with hexadecane in a 1:4 ratio to mimic a recycle operation around the deoxygenation reactor. The feed mixture was not further mixed or heated and was fed through the reactor inlet line by means of a piston pump where it was mixed with gaseous hydrogen. The hydrogen-crude tall oil-hexadecane mixture was then fed over the hydrogenation and deoxygenation catalyst in a downflow fixed bed reactor. The fixed bed reactor was maintained at 320° C., 500 psig, a H2/feed ratio of 2500 scf/bbl, and a LHSV of 1 h$^{-1}$ based on the crude tall oil portion of the feed only.

The initial appearance of the product was clear and colorless as expected for a deoxygenated hydrocarbon product. However, with each subsequent sample collected every 24 hours the product appearance became darker and increasingly opaque indicating incomplete deoxygenation and probable catalyst deactivation. The crude tall oil feed composition changed over time during this experiment with the heavy rosin acid components settling towards the bottom of the pump. Therefore, as the piston pump was gradually emptied the feed became increasingly rich in the rosin acid fraction which led to catalyst deactivation and incomplete deoxygenation as indicated by the product appearance over time. The table below shows the % deoxygenation of the feed over this run, demonstrating the deactivation of the catalyst with time. Post characterization of the feed showed naphthalenes and phenanthrenes were produced which are known to adsorb strongly and deactivate hydroprocessing catalysts.

TABLE 1

| | Day | | | | |
|---|---|---|---|---|---|
| | 1 | 2 | 3 | 4 | 5 |
| % Deoxygenation | 83% | 81% | 78% | 78% | 66% |

Example 2

Impact of Heating and Mixing on Feed Homogeneity

The crude tall oil feed was thoroughly mixed at room temperature and transferred to a Pyrex beaker. The room temperature appearance of the mixed crude tall oil feed showed an inhomogeneous mixture with small droplets of a dark brown phase dispersed in a black phase. After allowing to settle for 1 hour the feed separated with a brown phase appearing at the bottom with a much larger black phase above. This biphasic feed was heated on a hot plate to 50° C. with mixing. At 50° C. with mixing the mixture was homogeneous with no brown phase at the bottom or dispersed as droplets throughout. The temperature was increased to 60° C. with mixing and the crude tall oil remained homogeneous.

After the feed was cooled to room temperature and mixing was stopped, the crude tall oil again separated into two phases with the brown heavier phase at the bottom. The feed was again heated to 50° C. but this time without mixing. After holding the feed at 50° C. for one hour it still had a brown heavy phase visible at the bottom. The temperature was increased to 60° C. and kept at this temperature for 1 hour. After an hour the feed was homogeneous with no phase separation observed.

Example 3

Tall Oil Feed being Heated and Mixed

The crude tall oil thoroughly mixed, sampled, and then mixed with hexadecane in a 1:4 ratio to mimic a recycle operation around the deoxygenation reactor. The feed was mixed and heated at 70° C. before transferring to a piston pump that was heat traced to maintain a temperature of 70° C. in the pump. The hot feed was fed through the reactor inlet line by means of a piston pump where it was mixed with gaseous hydrogen The hydrogen-crude tall oil-hexadecane mixture was then fed over the hydrogenation and deoxygenation catalyst in a downflow fixed bed reactor. The fixed bed reactor temperature was varied throughout the run. The pressure was 1000 psig and the H2/feed ratio was 4000 scf/bbl. The LHSV, based on the crude tall oil portion of the feed only, was also varied throughout the run. The table below shows the varied reaction conditions and the production oxygen level. The hexadecane/CTO feed had an initial oxygen content of 1.8 wt % as measured by UOP 730: Total oxygen in liquid hydrocarbons by pyrolysis. The limit of detection for this method is 0.03 wt % oxygen.

This run ran for over 13 days without any sign of deactivation. The product remained clear and colorless throughout and full deoxygenation was achieved.

TABLE 2

| Period and hours on stream (HOS) | Conditions | Oxygen content of liquid product, hydrocarbon phase |
|---|---|---|
| 1 (3-16) | 0.75 LHSV, 338.5° C. | <0.03% |
| 2 (16-32) | 0.30 LHSV, 330.4° C. | <0.03% |
| 3 (32-40) | 0.75 LHSV, 338.0° C. | <0.03% |
| 4 (40-55) | 0.27 LHSV, 330.0° C. | <0.03% |
| 5 (58-64) | 0.75 LHSV, 338.5° C. | <0.03% |
| 6 (64-79) | 0.30 LHSV, 329.9° C. | <0.03% |
| 7 (79-82) | 0.75 LHSV, 338.9° C. | <0.03% |
| 8 (82-87) | 1.20 LHSV, 343.1° C. | <0.03% |
| 9 (87-114) | 0.75 LHSV, 341.8° C. | <0.03% |
| 10 (117-188) | 0.75 LHSV, 358.3° C. | <0.03% |
| 11 (189-261) | 0.75 LHSV, 387.9° C. | <0.03% |
| 12 (261-292) | 0.30 LHSV, 382.5° C. | <0.03% |
| 13 (292-322) | 0.75 LHSV, 341.2° C. | <0.03% |

The invention claimed is:

1. A process for producing a hydrocarbon product from a renewable feedstock comprising at least tall oil, said process comprising;
   a) heating the renewable feedstock comprising at least tall oil to a temperature of from about 60° C. to about 80° C.;
   b) conducting the renewable feedstock to a reaction zone while maintaining the temperature of the renewable feedstock at from about 60° C. to about 80° C.;
   c) treating the renewable feedstock in the reaction zone by hydrogenating and deoxygenating the feedstock at reaction conditions to provide a reaction product comprising paraffins having from about 8 to about 24 carbon atoms, and recycling a portion of the reaction product to the reaction zone wherein the volume ratio of recycle to feedstock is in the range of about 2:1 to about 8:1; and
   d) isomerizing at least a portion of the paraffins in the reaction product in an isomerization zone by contacting with an isomerization catalyst at isomerization conditions to isomerize at least a portion of the paraffins to branched-paraffins and generate the hydrocarbon product.

2. The process of claim 1 further comprising mixing the renewable feedstock before conducting the renewable feedstock to the reaction zone.

3. The process of claim 1 further comprising mixing the renewable feedstock at a temperature from about 60° C. to about 80° C. before conducting the renewable feedstock to the reaction zone.

4. The process of claim 1 wherein the volume ratio of recycle to feedstock is in the range of about 2:1 to about 6:1.

5. The process of claim 1 wherein the volume ratio of recycle to feedstock is in the range of about 4:1.

6. The process of claim 1 further comprising pre-treating the renewable feedstock in a pretreatment zone at pretreatment conditions to remove alkali metals.

7. The process of claim 1 where the feedstock is hydrogenated and deoxygenated by contacting the feedstock with a hydrogenation and deoxygenation catalyst at a temperature of about 200° C. to about 400° C. and a pressure of about 1379kPa absolute (200 psia) to about 10,342 kPa absolute (1500 psia).

8. The process of claim 1 wherein the reaction product is passed to the isomerization zone after separating a gaseous component from the reaction product.

9. The process of claim 1 where deoxygenation comprises at least one of decarboxylation, decarbonylation, and hydro-deoxygenation.

10. The process of claim 1 further comprising treating a petroleum hydrocarbon feedstock in the reaction zone.

11. The process of claim 1 wherein the renewable feedstock additionally comprises at least one component selected from the group consisting of canola oil, corn oil, soy oil, rapeseed oil, soybean oil, colza oil, sunflower oil, hempseed oil, olive oil, linseed oil, coconut oil, castor oil, peanut oil, palm oil, mustard oil, cottonseed oil, jatropha oil, camelina oil, tallow, yellow and brown greases, lard, train oil, fats in milk, fish oil, algal oil, sewage sludge.

12. The process of claim 11 wherein the renewable feedstock further comprises at least one co-feed component selected from the group consisting of spent motor oils, spent industrial lubricants, used paraffin waxes, liquids derived from the gasification of coal, biomass, natural gas followed by a downstream liquefaction step, liquids derived from depolymerization, thermal or chemical, of waste plastics, and synthetic oils generated as byproducts from petrochemical and chemical processes.

13. The process of claim 1 wherein the reaction zone and the isomerization zone are combined into a single stage.

14. The process of claim 1 further comprising blending at least a portion of the branched-paraffins with petroleum derived hydrocarbons to generate a blended fuel.

15. A process for producing a hydrocarbon product from a renewable feedstock comprising at least tall oil, said process comprising;
  a) heating the renewable feedstock comprising at least tall oil to a temperature of from about 60° C. to about 80° C.;
  b) conducting the renewable feedstock to a reaction zone while maintaining the temperature of the renewable feedstock at from about 60° C. to about 80° C.;
  c) treating the renewable feedstock in the reaction zone by hydrogenating and deoxygenating the feedstock at reaction conditions to provide a reaction product comprising paraffins having from about 16 to about 18 carbon atoms, and recycling a portion of the reaction product to the reaction zone wherein the volume ratio of recycle to feedstock is in the range of about 2:1 to about 8:1; and
  d) isomerizing at least a portion of the paraffins in the reaction product in an isomerization zone by contacting with an isomerization catalyst at isomerization conditions to isomerize at least a portion of the paraffins to branched-paraffins and generate the hydrocarbon product.

16. A process for producing a hydrocarbon product from a renewable feedstock comprising at least tall oil, said process comprising;
  a) heating the renewable feedstock comprising at least tall oil to a temperature of from about 60° C. to about 80° C.;
  b) conducting the renewable feedstock to a reaction zone while maintaining the temperature of the renewable feedstock at from about 60° C. to about 80° C.;
  c) treating the renewable feedstock in the reaction zone by hydrogenating and deoxygenating the feedstock at reaction conditions to provide a diesel boiling range hydrocarbon reaction product comprising paraffins having from about 16 to about 18 carbon atoms, and recycling a portion of the reaction product to the reaction zone wherein the volume ratio of recycle to feedstock is in the range of about 2:1 to about 8:1; and
  d) isomerizing at least a portion of the paraffins in the reaction product in an isomerization zone by contacting with an isomerization catalyst at isomerization conditions to isomerize at least a portion of the paraffins to branched-paraffins and generate the hydrocarbon product.

* * * * *